(12) United States Patent
Carelli et al.

(10) Patent No.: US 8,975,225 B2
(45) Date of Patent: Mar. 10, 2015

(54) METHOD FOR INHIBITING GROWTH OF CHONDROCYTES IN A SUBJECT BY INHIBITING IGF-1

(75) Inventors: Claude Carelli, Suresnes (FR); Zvi Laron, Ramat Efal (IL); Gila Maor, Kiriat-motzkin (IL)

(73) Assignee: Universite Pierre et Marie Curie (Paris 6), Paris (FR)

( * ) Notice: Subject to any disclaimer, the term of this patent is extended or adjusted under 35 U.S.C. 154(b) by 0 days.

(21) Appl. No.: 13/257,347

(22) PCT Filed: Mar. 19, 2009

(86) PCT No.: PCT/EP2009/053263
§ 371 (c)(1),
(2), (4) Date: Jan. 11, 2012

(87) PCT Pub. No.: WO2010/105685
PCT Pub. Date: Sep. 23, 2010

(65) Prior Publication Data
US 2012/0135926 A1    May 31, 2012

(51) Int. Cl.
| | |
|---|---|
| A61K 38/30 | (2006.01) |
| C07K 14/65 | (2006.01) |
| A61K 38/00 | (2006.01) |
| A61P 19/02 | (2006.01) |
| A61K 38/10 | (2006.01) |
| A61K 38/16 | (2006.01) |
| C07K 14/61 | (2006.01) |
| C07K 14/77 | (2006.01) |

(52) U.S. Cl.
CPC .............. *C07K 14/61* (2013.01); *C07K 14/65* (2013.01); *C07K 14/77* (2013.01); *A61K 38/00* (2013.01); *C07K 2319/00* (2013.01); *C07K 2319/74* (2013.01)
USPC ..................... 514/8.6; 514/16.8; 514/21.4

(58) Field of Classification Search
None
See application file for complete search history.

(56) References Cited

FOREIGN PATENT DOCUMENTS

| | | | |
|---|---|---|---|
| FR | 2833012 | * | 6/2003 |
| WO | 03/048206 | | 6/2003 |
| WO | 2006/075124 | | 7/2006 |

OTHER PUBLICATIONS

Gasparani, 2003, Trends in Neurosciences, vol. 26, Issue 8, pp. 404-406.*
Hall, 2012, Brain Research Bulletin, vol. 88, pp. 3-12.*
Torres-Aleman, 2007, Expert Opinion Therapy Targets, vol. 11, issue 12, pp. 1535-1542.*
Melmed, 2009, The Journal of Clinical Investigation, vol. 119, No. 11, pp. 3189-3202.*

* cited by examiner

*Primary Examiner* — Robert Landsman
(74) *Attorney, Agent, or Firm* — Cesari and McKenna, LLP

(57) ABSTRACT

The invention relates to peptides useful for inhibiting IGF-1 activity and their use as agents for inhibition of in vitrocell proliferation and for treatment of various diseases.

13 Claims, 2 Drawing Sheets

SEQUENCE LISTING

```
<160> NUMBER OF SEQ ID NOS: 25

<210> SEQ ID NO 1
<211> LENGTH: 38
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa can represent Arg, Ser, Asp, Ser, Thr, Ala,
      or Gly.
<220> FEATURE:
<221> NAME/KEY: MISC_FEATURE
<222> LOCATION: (2)..(2)
<223> OTHER INFORMATION: Xaa can represent Val, Asp, Arg, Ser, Thr, or
      Ala.
<220> FEATURE:
<221> NAME/KEY: MISC_FEATURE
<222> LOCATION: (3)..(3)
<223> OTHER INFORMATION: Xaa can represent Val, Asp, Arg, or Ser; or may
      be missing.
<220> FEATURE:
<221> NAME/KEY: MISC_FEATURE
<222> LOCATION: (4)..(4)
<223> OTHER INFORMATION: Xaa can represent Val, Asp, Arg, or Ser; or may
      be missing.
<220> FEATURE:
<221> NAME/KEY: MISC_FEATURE
<222> LOCATION: (5)..(5)
<223> OTHER INFORMATION: Xaa can represent Val, Asp, Arg, or Ser; or may
      be missing.
<220> FEATURE:
<221> NAME/KEY: MISC_FEATURE
<222> LOCATION: (6)..(6)
<223> OTHER INFORMATION: Xaa can represent Val or Asp; or may be
      missing.
<220> FEATURE:
<221> NAME/KEY: MISC_FEATURE
<222> LOCATION: (7)..(7)
<223> OTHER INFORMATION: Xaa can represent Val or may be missing.
<220> FEATURE:
<221> NAME/KEY: MISC_FEATURE
<222> LOCATION: (9)..(9)
<223> OTHER INFORMATION: Xaa can represent Glu or Asp.
<220> FEATURE:
<221> NAME/KEY: MISC_FEATURE
<222> LOCATION: (10)..(10)
<223> OTHER INFORMATION: Xaa can represent Lys, Ser, or Leu.
<220> FEATURE:
<221> NAME/KEY: MISC_FEATURE
<222> LOCATION: (14)..(14)
<223> OTHER INFORMATION: Xaa can represent Leu or may be missing.
<220> FEATURE:
<221> NAME/KEY: MISC_FEATURE
```

```
<222> LOCATION: (15)..(15)
<223> OTHER INFORMATION: Xaa can represent Glu or may be missing.
<220> FEATURE:
<221> NAME/KEY: MISC_FEATURE
<222> LOCATION: (16)..(16)
<223> OTHER INFORMATION: Xaa can represent Glu or may be missing.
<220> FEATURE:
<221> NAME/KEY: MISC_FEATURE
<222> LOCATION: (17)..(17)
<223> OTHER INFORMATION: Xaa can represent Gly or may be missing.
<220> FEATURE:
<221> NAME/KEY: MISC_FEATURE
<222> LOCATION: (18)..(18)
<223> OTHER INFORMATION: Xaa can represent Ile or may be missing.
<220> FEATURE:
<221> NAME/KEY: MISC_FEATURE
<222> LOCATION: (19)..(19)
<223> OTHER INFORMATION: Xaa can represent Gln or may be missing.
<220> FEATURE:
<221> NAME/KEY: MISC_FEATURE
<222> LOCATION: (20)..(20)
<223> OTHER INFORMATION: Xaa can represent Ala or Thr or may be missing.
<220> FEATURE:
<221> NAME/KEY: MISC_FEATURE
<222> LOCATION: (21)..(21)
<223> OTHER INFORMATION: Xaa can represent Leu or may be missing.
<220> FEATURE:
<221> NAME/KEY: MISC_FEATURE
<222> LOCATION: (24)..(24)
<223> OTHER INFORMATION: Xaa can represent Cys, Ser, Tyr, Phe, Asp, Glu,
    Ala, or Gly.
<220> FEATURE:
<221> NAME/KEY: MISC_FEATURE
<222> LOCATION: (29)..(29)
<223> OTHER INFORMATION: Xaa can represent Trp.
<220> FEATURE:
<221> NAME/KEY: MISC_FEATURE
<222> LOCATION: (30)..(30)
<223> OTHER INFORMATION: Xaa can represent Lys.
<220> FEATURE:
<221> NAME/KEY: MISC_FEATURE
<222> LOCATION: (31)..(31)
<223> OTHER INFORMATION: Xaa can represent Thr or may be missing.
<220> FEATURE:
<221> NAME/KEY: MISC_FEATURE
<222> LOCATION: (32)..(32)
<223> OTHER INFORMATION: Xaa can represent Phe or may be missing.
<220> FEATURE:
<221> NAME/KEY: MISC_FEATURE
<222> LOCATION: (33)..(33)
<223> OTHER INFORMATION: Xaa can represent Thr or may be missing.
<220> FEATURE:
<221> NAME/KEY: MISC_FEATURE
<222> LOCATION: (34)..(34)
<223> OTHER INFORMATION: Xaa can represent Ser or may be missing.
<220> FEATURE:
<221> NAME/KEY: MISC_FEATURE
<222> LOCATION: (35)..(35)
<223> OTHER INFORMATION: Xaa can represent Cys, Ser, Tyr, Phe, Asp, Glu,
    Ala, or Gly; or may be missing.
<220> FEATURE:
<221> NAME/KEY: MISC_FEATURE
<222> LOCATION: (36)..(36)
<223> OTHER INFORMATION: Xaa can represent Lys or may be missing.
<220> FEATURE:
<221> NAME/KEY: MISC_FEATURE
<222> LOCATION: (37)..(37)
<223> OTHER INFORMATION: Xaa can represent Gln or may be missing.
<220> FEATURE:
<221> NAME/KEY: MISC_FEATURE
<222> LOCATION: (38)..(38)
<223> OTHER INFORMATION: Xaa can represent Ala or may be missing.

<400> SEQUENCE: 1

Xaa Xaa Xaa Xaa Xaa Xaa Xaa Tyr Xaa Xaa Leu Lys Asp Xaa Xaa Xaa
1               5                   10                  15

Xaa Xaa Xaa Xaa Xaa Ala Gly Xaa Lys Asn Phe Phe Xaa Xaa Xaa Xaa
```

```
            20                  25                  30
Xaa Xaa Xaa Xaa Xaa Xaa
        35

<210> SEQ ID NO 2
<211> LENGTH: 24
<212> TYPE: PRT
<213> ORGANISM: artificial sequence
<220> FEATURE:
<223> OTHER INFORMATION: Synthetic polypeptide

<400> SEQUENCE: 2

Gly Thr Ser Asp Arg Val Tyr Glu Lys Leu Ala Gly Ser Lys Asn Phe
1               5                   10                  15

Phe Trp Lys Thr Phe Thr Ser Ser
            20

<210> SEQ ID NO 3
<211> LENGTH: 25
<212> TYPE: PRT
<213> ORGANISM: artificial sequence
<220> FEATURE:
<223> OTHER INFORMATION: Synthetic polypeptide

<400> SEQUENCE: 3

Gly Ala Ser Asp Ser Asp Val Tyr Asp Leu Leu Ala Gly Ser Lys Asn
1               5                   10                  15

Phe Phe Trp Lys Thr Phe Thr Ser Ser
            20                  25

<210> SEQ ID NO 4
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: Xaa can represent Arg or Ser.
<220> FEATURE:
<221> NAME/KEY: MISC_FEATURE
<222> LOCATION: (4)..(4)
<223> OTHER INFORMATION: Xaa can represent Val or Asp.
<220> FEATURE:
<221> NAME/KEY: MISC_FEATURE
<222> LOCATION: (5)..(5)
<223> OTHER INFORMATION: Xaa can represent Val or may be missing.

<400> SEQUENCE: 4

Ser Asp Xaa Xaa Xaa
1               5

<210> SEQ ID NO 5
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa can represent Thr or Ala.
<220> FEATURE:
<221> NAME/KEY: MISC_FEATURE
<222> LOCATION: (4)..(4)
<223> OTHER INFORMATION: Xaa can represent Arg or Ser.
<220> FEATURE:
<221> NAME/KEY: MISC_FEATURE
```

```
<222> LOCATION: (5)..(5)
<223> OTHER INFORMATION: Xaa can represent Val or Asp.

<400> SEQUENCE: 5

Xaa Ser Asp Xaa Xaa
1               5

<210> SEQ ID NO 6
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa can represent Thr or Ala.
<220> FEATURE:
<221> NAME/KEY: MISC_FEATURE
<222> LOCATION: (5)..(5)
<223> OTHER INFORMATION: Xaa can represent Arg or Ser.
<220> FEATURE:
<221> NAME/KEY: MISC_FEATURE
<222> LOCATION: (6)..(6)
<223> OTHER INFORMATION: Xaa can represent Val or Asp.
<220> FEATURE:
<221> NAME/KEY: MISC_FEATURE
<222> LOCATION: (7)..(7)
<223> OTHER INFORMATION: Xaa can represent Val or may be missing.

<400> SEQUENCE: 6

Gly Xaa Ser Asp Xaa Xaa Xaa
1               5

<210> SEQ ID NO 7
<211> LENGTH: 4
<212> TYPE: PRT
<213> ORGANISM: artificial sequence
<220> FEATURE:
<223> OTHER INFORMATION: Synthetic polypeptide

<400> SEQUENCE: 7

Lys Asp Leu Glu
1

<210> SEQ ID NO 8
<211> LENGTH: 5
<212> TYPE: PRT
<213> ORGANISM: artificial sequence
<220> FEATURE:
<223> OTHER INFORMATION: Synthetic polypeptide

<400> SEQUENCE: 8

Lys Asp Leu Glu Glu
1               5

<210> SEQ ID NO 9
<211> LENGTH: 6
<212> TYPE: PRT
<213> ORGANISM: artificial sequence
<220> FEATURE:
<223> OTHER INFORMATION: Synthetic polypeptide

<400> SEQUENCE: 9

Lys Asp Leu Glu Glu Gly
1               5

<210> SEQ ID NO 10
<211> LENGTH: 7
```

```
<212> TYPE: PRT
<213> ORGANISM: artificial sequence
<220> FEATURE:
<223> OTHER INFORMATION: Synthetic polypeptide

<400> SEQUENCE: 10

Lys Asp Leu Glu Glu Gly Ile
1               5

<210> SEQ ID NO 11
<211> LENGTH: 8
<212> TYPE: PRT
<213> ORGANISM: artificial sequence
<220> FEATURE:
<223> OTHER INFORMATION: Synthetic polypeptide

<400> SEQUENCE: 11

Lys Asp Leu Glu Glu Gly Ile Gln
1               5

<210> SEQ ID NO 12
<211> LENGTH: 9
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (9)..(9)
<223> OTHER INFORMATION: Xaa can represent Ala or Thr

<400> SEQUENCE: 12

Lys Asp Leu Glu Glu Gly Ile Gln Xaa
1               5

<210> SEQ ID NO 13
<211> LENGTH: 10
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (9)..(9)
<223> OTHER INFORMATION: Xaa can represent Ala or Thr.

<400> SEQUENCE: 13

Lys Asp Leu Glu Glu Gly Ile Gln Xaa Leu
1               5                   10

<210> SEQ ID NO 14
<211> LENGTH: 4
<212> TYPE: PRT
<213> ORGANISM: artificial sequence
<220> FEATURE:
<223> OTHER INFORMATION: Synthetic polypeptide

<400> SEQUENCE: 14

Trp Lys Thr Phe
1

<210> SEQ ID NO 15
<211> LENGTH: 5
<212> TYPE: PRT
<213> ORGANISM: artificial sequence
<220> FEATURE:
<223> OTHER INFORMATION: Synthetic polypeptide

<400> SEQUENCE: 15
```

```
Trp Lys Thr Phe Thr
1               5

<210> SEQ ID NO 16
<211> LENGTH: 6
<212> TYPE: PRT
<213> ORGANISM: artificial sequence
<220> FEATURE:
<223> OTHER INFORMATION: Synthetic polypeptide

<400> SEQUENCE: 16

Trp Lys Thr Phe Thr Ser
1               5

<210> SEQ ID NO 17
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (7)..(7)
<223> OTHER INFORMATION: Xaa can represent Cys, Ser, Tyr, Phe, Asp, Glu,
      Ala, or Gly.

<400> SEQUENCE: 17

Trp Lys Thr Phe Thr Ser Xaa
1               5

<210> SEQ ID NO 18
<211> LENGTH: 10
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (7)..(7)
<223> OTHER INFORMATION: Xaa can represent Cys, Ser, Tyr, Phe, Asp, Glu,
      Ala, or Gly.

<400> SEQUENCE: 18

Trp Lys Thr Phe Thr Ser Xaa Lys Gln Ala
1               5                   10

<210> SEQ ID NO 19
<211> LENGTH: 4
<212> TYPE: PRT
<213> ORGANISM: Artificial sequence
<220> FEATURE:
<223> OTHER INFORMATION: Synthetic polypeptide

<400> SEQUENCE: 19

Asp Ser Asp Val
1

<210> SEQ ID NO 20
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa can represent Thr or Ala.
<220> FEATURE:
<221> NAME/KEY: MISC_FEATURE
```

```
<222> LOCATION: (5)..(5)
<223> OTHER INFORMATION: Xaa can represent Arg or Ser.
<220> FEATURE:
<221> NAME/KEY: MISC_FEATURE
<222> LOCATION: (6)..(6)
<223> OTHER INFORMATION: Xaa can represent Val or Asp.
<220> FEATURE:
<221> NAME/KEY: MISC_FEATURE
<222> LOCATION: (7)..(7)
<223> OTHER INFORMATION: Xaa can represent Val or may be missing.

<400> SEQUENCE: 20

Gly Xaa Ser Asp Xaa Xaa Xaa
1               5

<210> SEQ ID NO 21
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (7)..(7)
<223> OTHER INFORMATION: Xaa can represent Cys, Ser, Tyr, Phe, Asp, Glu,
      Ala, or Gly

<400> SEQUENCE: 21

Trp Lys Thr Phe Thr Ser Xaa
1               5

<210> SEQ ID NO 22
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 22

Gly Thr Ser Asp Arg Val
1               5

<210> SEQ ID NO 23
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 23

Gly Ala Ser Asp Ser Asp Val
1               5

<210> SEQ ID NO 24
<211> LENGTH: 24
<212> TYPE: PRT
<213> ORGANISM: Artificial sequence
<220> FEATURE:
<223> OTHER INFORMATION: Synthetic polypeptide
<220> FEATURE:
<221> NAME/KEY: MOD_RES
<222> LOCATION: (1)..(1)
<223> OTHER INFORMATION: N-terminal ACETYLATION

<400> SEQUENCE: 24

Gly Thr Ser Asp Arg Val Tyr Glu Lys Leu Ala Gly Ser Lys Asn Phe
1               5                   10                  15

Phe Trp Lys Thr Phe Thr Ser Ser
            20
```

```
<210> SEQ ID NO 25
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 25

Trp Lys Thr Phe Thr Ser Ser
1               5
```

METHOD FOR INHIBITING GROWTH OF CHONDROCYTES IN A SUBJECT BY INHIBITING IGF-1

CROSS REFERENCE TO RELATED APPLICATIONS

This application claims the priority of international application no. PCT/EP2009/053263, filed on Mar. 19, 2009, the contents of which are incorporated by reference.

The invention related to peptides for the inhibition of IGF-1 activities.

BACKGROUND OF THE INVENTION

Carcinogenesis is commonly related to the loss of cell quiescence and the abrogation of cell division control, provoking uncontrolled cell proliferation and biomass increase. Proliferation is a complex process, but a key element is overexpression of growth factors and/or their receptors in the cell (Moyse et al. 1985, Cassoni et al. 2006, Hanahan et al. 2000). Normally, these protein pathways, collectively termed 'signal transduction', are tightly controlled. Deregulation of signaling pathway gives rise to the progression of oncogenic transformation and tumorigenesis. All cancer cells exhibit a deregulated cell cycle, leading to the evolution of cells which can evade cancer therapies. Many factors acting as a network are involved in cell cycle progression and cell proliferation. In particular, growth factors are capable of stimulating entry into S phase of the cell cycle and therefore, cell division.

Among those, Insulin-like growth factors (IGFs) are important mediators of growth, development, and survival. They are synthesized by almost any tissue in the body. The action of IGFs is modulated by a complex network of molecules, including binding proteins, proteases and receptors, which all comprise the "IGF system".

IGF-1, among others, which synthesis is activated by GH, acts as an endocrine hormone and could be considered as the actual growth hormone (Laron, 2001). The effect of IGF-1 can also be mediated by paracrine/autocrine mechanism. In children, IGF-1 stimulates growth whereas in adults, it increases anabolism. IGF-1 is a peptide that binds IGF-1 receptor (IGF-1R), a membrane receptor expressed in various tissues, e.g. liver, kidney, lung, muscles, bone, nervous and cartilaginous tissues. Activation of IGFR-1 by IGF-1 is implicated in cell survival, growth, proliferation, differentiation, and migration in epithelial and mesenchymal tissues (Perona, 2006). The activation of the IGF-1 receptor by suitable ligand plays a central role in the proliferation of most cell types. Evidence from in vitro and animal studies suggests that overexpression of IGF-1 by cancer cells and/or the nearby stroma as well as the IGF-1 receptors by the cancer cells plays a significant role in establishing a transformed phenotype in an increasing number of malignancies. More specifically, IGF-1 promotes protein synthesis and inhibition of apoptosis (programmed cell death) (Yanochko et al 2006, Colòn et al 2007, Inoue et al 2005).

The role of IGF-1 signaling network in carcinogenesis and tumor progression, including metastatic processes, is established (Hofmann et al 2005). In addition, a growing number of epidemiologic studies suggest that increased serum levels of IGF-1 and/or altered expression of their receptors are associated with increased risk for developing cancer (Vella et al 2001, Talapatra et al 2001, Kucab et al 2003, Kambhampati et al 2005, Bjorndahl et al 2005, Gennigens et al 2006, Velcheti et al 2006, Sisci et al 2007, Samani et al 2007). The critical role of IGF-1/GH axis in oncogenesis and stimulation of tumor progression is suggested in various studies, particularly in a recent study describing an IGF-1 congenital deficiency that could prevent from cancer development (Sheva et al 2007).

These data indicate that IGF dysregulation should now be considered as a potential target for novel antineoplastic therapies and/or preventative strategies in high-risk groups. Accordingly, clinical studies have been carried out on inhibitors of IGF-1 activities and indicate potential interest of their use in various type of cancer (Min et al 2005, Camirand et al 2005, Chinnavian et al 2006, Wu et al 2006, Deutsh et al 2005, Warshamana-Greene et al 2005). Since IGF-1 is the principal mediator of GH, IGF-1 production can be decreased or inhibited upstream GH production, with Somatostatin for example.

Somatostatin (*Somatotrope Release Inhibiting Factor* or SRIF) was known for its effect of inhibiting GH secretion. Indeed, somatostatin is a growth hormone-releasing hormone (GHRH) antagonist. Somatostatin and GHRH are both secreted by hypothalamic neurons and controlled GH secretion. SRIF has an indirect effect on IGF-1 synthesis by inhibiting GH. SRIF also has a peripheral action: it has been shown to inhibit gastrointestinal and pancreatic hormones secretion.

Several therapeutic protocols use the SRIF and synthetic analogs capacity to inhibit cell proliferation and cell death induction to treat different types of cancer. Moreover, SRIF can inhibit angiogenesis mediated by Vascular Endothelial Growth Factor (VEGF), thus representing a potential clinical interest for the control of tumor growth (Ferjoux et al 2000, Dasgupta 2004, Garcia de la Torre et al. 2002).

However, SRIF analogs are useful in treatment of tumor expressing SRIF receptors only. SRIF receptors have been identified in a variety of human tumors and cancer etiology is associated with an alteration in SRIF receptor expression pattern in many instances. Efficiency of SRIF analogs has already been assessed for neuroendocrinic, gastroenteropancreatic, brain, breast, prostatic and lung tumors treatment (Ferjoux et al 2000). Besides, one should bear in mind that SRIF receptors levels and expression pattern greatly differ from one carcinoma to another.

Different somatostatin analogs useful as "IGFs system" inhibitors have been proposed (Pawlikowski M. et al., 2004), namely BIM 23A387, octreotide or lanreotide. These molecules allow effective modulation of receptors or ligand expression and could be considered as new candidate drugs for cancer and acromegaly treatments. Other example is bispecific ligand BIM-23244, which is able to suppress GH secretion in somatotropic adenoma (Rani C., 2004, Rani C., 2006, Pandit A., 2008).

International patent application WO03/048206 discloses chimeric peptides that potentiate GH activity and their use for stimulating cell proliferation.

SUMMARY OF THE INVENTION

The inventors have now shown that chimeric peptides has described in WO03/048206 displayed a bi-phasic effect response, with enhancing effects at low doses, and inhibitory effects when added at high peptides concentration. The present invention thus relates to peptides for indirect antagonization of GH activities. More particularly, these antagonists are able to decrease IGF-1 activities as well as the growth of several different cell types, including adenoma cells and chondrocytes. On this basis, the inventors propose to use these peptides as inhibitors of IGF-1 activity in cells expressing IGF-1 and/or IGF-1 receptors, or for inhibition of cell proliferation in vitro, or for treatment of various diseases and as somatostatin's substitute. Indeed, the peptides described herein show great potential both as inhibitors of the structure/function activities of the IGF-1 signaling pathway and as novel clinical strategies in controlling abnormal cellular proliferation.

The peptides for inhibition of IGF-1 system comprise the following amino acids sequence:

(I) (SEQ ID NO: 1)
$X_1$-Tyr-$X_2$-Leu-$X_3$-Ala-Gly-$X_4$-Lys-Asn-Phe-Phe-$X_5$ wherein:

$X_1$ is vacant or is valine or a sequence selected from:

$Z_1$-Val

Asp-Arg-Val

Asp-Ser-Asp-Val (SEQ ID NO: 19)

Ser-Asp-$Z_1$-Val (SEQ ID NO: 4)

$Z_2$-Ser-Asp-$Z_1$-Val, (SEQ ID NO: 5)
and

Gly-$Z_2$-Ser-Asp-$Z_1$-Val (SEQ ID NO: 6)

wherein $Z_1$ is arginine and $Z_2$ threonine, or $Z_1$ is Ser-Asp, and $Z_2$ is alanine;

$X_2$ is a sequence selected from Glu-Lys, Glu-Ser and Asp-Leu;

$X_3$ is vacant or is lysine or a sequence selected from:

Lys-Asp

Lys-Asp-Leu

Lys-Asp-Leu-Glu (SEQ ID NO: 7)

Lys-Asp-Leu-Glu-Glu (SEQ ID NO: 8)

Lys-Asp-Leu-Glu-Glu-Gly (SEQ ID NO: 9)

Lys-Asp-Leu-Glu-Glu-Gly-Ile (SEQ ID NO: 10)

Lys-Asp-Leu-Glu-Glu-Gly-Ile-Gln (SEQ ID NO: 11)

Lys-Asp-Leu-Glu-Glu-Gly-Ile-Gln-$Z_3$, (SEQ ID NO: 12)
and

Lys-Asp-Leu-Glu-Glu-Gly-Ile-Gln-$Z_3$-Leu (SEQ ID NO: 13)

wherein $Z_3$ is alanine or threonine;

$X_4$ is an amino acid residue selected from cysteine, serine, tyrosine, phenylalanine, aspartic acid, glutamic acid, alanine and glycine; and $X_5$ is vacant or is a tryptophan residue or a sequence selected from:

Trp-Lys

Trp-Lys-Thr

Trp-Lys-Thr-Phe (SEQ ID NO: 14)

Trp-Lys-Thr-Phe-Thr (SEQ ID NO: 15)

Trp-Lys-Thr-Phe-Thr-Ser (SEQ ID NO: 16)

Trp-Lys-Thr-Phe-Thr-Ser-$X_6$, (SEQ ID NO: 17)
and

Trp-Lys-Thr-Phe-Thr-Ser-$X_6$-Lys-Gln-Ala (SEQ ID NO: 18)

wherein $X_6$ is an amino acid residue selected from cysteine, serine, tyrosine, phenylalanine, aspartic acid, glutamic acid, alanine and glycine.

Also encompassed are proteolysis-resistant peptides deriving from sequence (I) by one or more chemical modifications, or substantially homologous peptides deriving from sequence (I) by one or more conservative substitutions.

DETAILED DESCRIPTION OF THE INVENTION

Definitions

The term "inhibition" means here an inhibitory action on IGF-1 function. The inhibitory activity of a peptide on the IGF-1 activity and/or function can be studied for example by IGF-1 and/or IGF-1R expression assay. The inhibition of the peptides can also be studied by using cultured cells expressing the IGF-1 and/or IGF-1R. The term "inhibition" includes also inhibition and/or down-regulation reducing the activity, activation, function and/or expression of IGF-1.

The term "patient" refers to a human or non human animal, preferably a mammal, including male, female, adult and children in need of a treatment wherein inhibition of IGF-1 synthesis and/or expression of IGF-1 receptor is desired.

As used herein, the term "treatment" or "therapy" includes curative and/or prophylactic treatment. More particularly, curative treatment refers to any of the alleviation, amelioration and/or elimination, reduction and/or stabilization (e.g., failure to progress to more advanced stages) of a symptom, as well as delay in progression of a symptom of a particular disorder.

Prophylactic treatment refers to any of: halting the onset, reducing the risk of development, reducing the incidence, delaying the onset, reducing the development, as well as increasing the time to onset of symptoms of a particular disorder.

The term "conservative substitution" as used herein denotes the replacement of an amino acid residue by another, without altering the overall conformation and function of the peptide, including, but not limited to, replacement of an amino acid with one having similar properties (such as, for example, polarity, hydrogen bonding potential, acidic, basic, shape, hydrophobic, aromatic, and the like). Amino acids with similar properties are well known in the art. For example, arginine, histidine and lysine are hydrophilic-basic amino acids and may be interchangeable. Similarly, isoleucine, a hydrophobic amino acid, may be replaced with leucine, methionine or valine. Neutral hydrophilic amino acids, which can be substituted for one another, include asparagine, glutamine, serine and threonine. By "substituted" or "modified" the present invention includes those amino acids that have been altered or modified from naturally occurring amino acids.

As such, it should be understood that in the context of the present invention, a conservative substitution is recognized in the art as a substitution of one amino acid for another amino acid that has similar properties. Examples of conservative substitutions are set out in the Table 1 below:

TABLE 1

Conservative Substitutions I

| SIDE CHAIN CHARACTERISTIC | AMINO ACID |
|---|---|
| Non polar | G A P I L V |
| Polar-uncharged | C S T M N Q |
| Polar-charged | D E K R |
| Aromatic | H F W Y |
| Other | N Q D E |

Alternatively, conservative amino acids can be grouped as described in Lehninger, 1975, as set out in Table 2, immediately below.

TABLE 2

Conservative Substitutions II

| SIDE CHAIN CHARACTERISTIC | AMINO ACID |
|---|---|
| Non-polar (hydrophobic) | |
| A. Aliphatic: | A L I V P |
| B. Aromatic: | F W |
| C. Sulfur-containing: | M |
| D. Borderline: | G |
| Uncharged-polar | |
| A. Hydroxyl: | S T Y |
| B. Amides: | N Q |
| C. Sulfhydryl: | C |
| D. Borderline: | G |
| Positively Charged (Basic): | K R H |
| Negatively Charged (Acidic): | D E |

As still another alternative, exemplary conservative substitutions are set out in Table 3, immediately below.

TABLE 3

Conservative Substitutions III

| Original Residue | Exemplary Substitution |
|---|---|
| Ala (A) | Val (V), Leu (L), Ile (I) |
| Arg (R) | Lys (K), Gln (Q), Asn (N) |
| Asn (N) | Gln (Q), His (H), Lys (K), Arg (R) |

TABLE 3-continued

Conservative Substitutions III

| Original Residue | Exemplary Substitution |
|---|---|
| Asp (D) | Glu (E) |
| Cys (C) | Ser (S) |
| Gln (Q) | Asn (N) |
| Glu (E) | Asp (D) |
| His (H) | Asn (N), Gln (Q), Lys (K), Arg (R) |
| Ile (I) | Leu (L), Val (V), Met (M), Ala (A), Phe (F) |
| Leu (L) | Ile (I), Val (V), Met (M), Ala (A), Phe (F) |
| Lys (K) | Arg (R), Gln (Q), Asn (N) |
| Met (M) | Leu (L), Phe (F), Ile (I) |
| Phe (F) | Leu (L), Val (V), Ile (I), Ala (A) |
| Pro (P) | Gly (G) |
| Ser (S) | Thr (T) |
| Thr (T) | Ser (S) |
| Trp (W) | Tyr (T) |
| Tyr (Y) | Trp (W), Phe (F), Thr (T), Ser (S) |
| Val (V) | Ile (I), Leu (L), Met (M), Phe (F), Ala (A) |

Peptide Preparation:

Peptides described herein can be synthesized using standard synthetic methods known to those skilled in the art, for example chemical synthesis or genetic recombination. In a preferred embodiment, peptides are obtained by stepwise condensation of amino acids residue, either by condensation of a preformed fragment already containing an amino acid sequence in appropriate order, or by condensation of several fragments previously prepared, while protecting the amino acid functional groups except those involved in peptide bond during condensation. In particular, the peptides can be synthesized according to the method originally described by Merrifield.

Peptide Characteristics:

The peptides useful in the invention are synthetic peptides deriving from a chimeric synthetic sequence consisting of a fragment of growth hormone sequence linked via an amino bond to a fragment of somatostatin sequence.

According to one embodiment, peptides useful in the invention comprise, or consist in the following amino acid sequence:

(I)

(SEQ ID NO: 1)

$X_1$-Tyr-$X_2$-Leu-$X_3$-Ala-Gly-$X_4$-Lys-Asn-Phe-Phe-$X_5$ wherein:
$X_1$ is vacant or is valine or a sequence selected from:

```
Z₁-Val

Asp-Arg-Val

Asp-Ser-Asp-Val          (SEQ ID NO: 19)

Ser-Asp-Z₁-Val           (SEQ ID NO: 4)

Z₂-Ser-Asp-Z₁-Val, and   (SEQ ID NO: 5)

Gly-Z₂-Ser-Asp-Z₁-Val    (SEQ ID NO: 6)
``` wherein $Z_1$ is arginine and $Z_2$ threonine, or $Z_1$ is Ser-Asp, and $Z_2$ is alanine;
$X_2$ is a sequence selected from Glu-Lys, Glu-Ser and Asp-Leu;
$X_3$ is vacant or is lysine or a sequence selected from:

```
Lys-Asp

Lys-Asp-Leu

Lys-Asp-Leu-Glu

Lys-Asp-Leu-Glu-Glu                      (SEQ ID NO: 8)

Lys-Asp-Leu-Glu-Glu-Gly                  (SEQ ID NO: 9)

Lys-Asp-Leu-Glu-Glu-Gly-Ile              (SEQ ID NO: 10)

Lys-Asp-Leu-Glu-Glu-Gly-Ile-Gln          (SEQ ID NO: 11)

Lys-Asp-Leu-Glu-Glu-Gly-Ile-Gln-Z₃,      (SEQ ID NO: 12)
and

Lys-Asp-Leu-Glu-Glu-Gly-Ile-Gln-Z₃-Leu   (SEQ ID NO: 13)
``` wherein $Z_3$ is alanine or threonine;
$X_4$ is an amino acid residue selected from cysteine, serine, tyrosine, phenylalanine, aspartic acid, glutamic acid, alanine and glycine; and
$X_5$ is vacant or is a tryptophan residue or a sequence selected from:

```
Trp-Lys

Trp-Lys-Thr

Trp-Lys-Thr-Phe                    (SEQ ID NO: 14)

Trp-Lys-Thr-Phe-Thr                (SEQ ID NO: 15)

Trp-Lys-Thr-Phe-Thr-Ser            (SEQ ID NO: 16)

Trp-Lys-Thr-Phe-Thr-Ser-X₆,        (SEQ ID NO: 17)
and

Trp-Lys-Thr-Phe-Thr-Ser-X₆-Lys-Gln-Ala   (SEQ ID NO: 18)
``` wherein $X_6$ is an amino acid residue selected from cysteine, serine, tyrosine, phenylalanine, aspartic acid, glutamic acid, alanine and glycine;
In a preferred embodiment in sequence (I), $X_1$ is sequence Gly-$Z_2$-Ser-Asp-$Z_1$-Val (SEQ ID NO: 20) wherein $Z_1$ and $Z_2$ are as described above, $X_3$ is vacant, $X_2$ and $X_4$ are as described above, and $X_5$ is sequence Trp-Lys-Thr-Phe-Thr-Ser-$X_6$ (SEQ ID NO: 21) wherein $X_6$ is as described above.
In a first aspect of the preferred embodiment, in sequence (I) $X_1$ is Gly-Thr-Ser-Asp-Arg-Val (SEQ ID NO: 22), $X_2$ is sequence Glu-Lys, and $X_4$ and $X_6$ are both a serine residue, leading to the peptide of the following amino acids sequence (II):

```
                                                    (SEQ ID NO: 2)
Gly-Thr-Ser-Asp-Arg-Val-Tyr-Glu-Lys-Leu-Ala-Gly-Ser-Lys-Asn-Phe-Phe-Trp-

Lys-Thr-Phe-Thr-Ser-Ser (II)
```

In a particular embodiment of the invention, in sequence (I), $X_1$ is sequence Gly-Ala-Ser-Asp-Ser-Asp-Val (SEQ ID NO: 23), $X_2$ is sequence Asp-Leu and $X_4$ and $X_6$ are both serine residue leading to peptide comprises the following amino acids sequence (III):

```
                                                    (SEQ ID NO: 3)
Gly-Ala-Ser-Asp-Ser-Asp-Val-Tyr-Asp-Leu-Leu-Ala-Gly-Ser-Lys-Asn-Phe-Phe-

Trp-Lys-Thr-Phe-Thr-Ser-Ser (III)
```

The N- and C-termini of the peptides described herein may be optionally protected against proteolysis. For instance, the N-terminus may be in the form of an acetyl group, and/or the C-terminus may be in the form of an amide group. Internal modifications of the peptides to be resistant to proteolysis are also envisioned, e.g. wherein at least a —CONH-peptide bond is modified and replaced by a (CH2NH) reduced bond, a (NHCO) retro-inverso bond, a (CH2-O) methylene-oxy bond, a (CH2-S) thiomethylene bond, a (CH2CH2) carba bond, a (CO—CH2) cetomethylene bond, a (CHOH—CH2) hydroxyethylene bond), a (N—N) bound, a E-alcene bond or also a —CH═CH-bond.

All these proteolysis-resistant chemically-modified peptides are encompassed in the present invention.

Also encompassed are substantially homologous peptides deriving from sequence (I) by one or more conservative substitution. Preferably, these homologous peptides do not include two cysteine residues, so that cyclization is prevented. Two amino acid sequences are "substantially homologous" or "substantially similar" when one or more amino acid residue are replaced by a biologically similar residue or when greater than 80% of the amino acids are identical, or greater than about 90%, preferably greater than about 95%, are similar (functionally identical). Preferably, the similar or homologous sequences are identified by alignment using, for example, the GCG (Genetics Computer Group, Program Manual for the GCG Package, Version 7, Madison, Wis.) pileup program, or any of the programs known in the art (BLAST, FASTA, etc.).

According to the invention, all amino acid residues belong to the L form. However, it is preferred that threonine, alanine and tryptophane and phenylalanine residues, particularly the two contiguous phenylalanines of the peptides—said residues being on position 20 and 22 in sequence (II) and (III)—belong to the D form, for the peptide to be more resistant to peptidases.

Furthermore, tryptophane residue of the peptides—when $X_5$ is in sequence (I), thus being in position 18 in sequences (II) and (III)—can be linked to a $C_1$-$C_3$ alkyl group (methyl, ethyl, propyl, isopropyl) for the peptides to resist to oxidation.

In another aspect of the invention, peptides are covalently bound to a polyethylene glycol (PEG) molecule by their C-terminal terminus or a lysine residue, notably a PEG of 1500 or 4000 MW, for a decrease in urinary clearance and in therapeutic doses used and for an increase of the half-life in blood plasma. The binding of PEG is as described by Abu-chowski et al. (J. Biol. Chenu., 1977, 252: 3582-3586). In a further aspect of the invention, two or more PEG molecules are bound in each anchorage site. In yet another embodiment, peptide half-life is increased by including the peptide in a biodegradable and biocompatible polymer material for drug delivery system forming microspheres. Polymers and copolymers are, for instance, poly(D,L-lactide-co-glycolide) (PLGA) (as illustrated in US2007/0184015, SoonKap Hahn et al).

Advantageously, even when administered in an iterate way, peptides described herein do not induce anti-peptide or anti-GH antibody production, in contrast with immunogenic peptides of the art, which cause antibody production leading to endogenous GH neutralization and thus, to biological activity neutralization.

Peptides are shown to have no toxic effect.

Peptides differ from endogenous somatostatin or from peptides known in the art and exhibit a β-hairpin molecular conformation which stability depends of physiological medium and hydrophobic medium used. Furthermore, the β-hairpin conformation allows peptides of the invention to adapt and to bind with a great affinity to SRIF receptors.

Peptides useful herein display bi-phasic effect to IGF-1 production and/or IGF-1 expression receptor with enhancing/stimulatory effects when added at low doses, and inhibitory effect when added at high peptide concentration. Bi-phasic effect of a biological molecule showing a dose dependent agonist or antagonist effect is well known for other molecules and in various biological systems (enzymes [Gamage et al. 2003, He et al. 2003], ionic channels and co-carriers [Arias et al. 1996, Lombardi et al. 2001, Borst et al. 2002, Incerpi et al. 2003] carriers [Henry et al. 2002], tyrosine kinase receptors [Leiser et al. 1986, Schlessinger 1988], G protein-coupled receptor (GPCRs), neurotransmitters, hormones and chemokines [Winding et al. 1993, Chidiac et al. 1996, Bronnikov et al. 1999, Cuthbert 2003, Hornigold et al. 2003, Griffin et al. 2003, Fuh et al. 1992, Talmadge 1998], in particular concerning GnRH and analogs thereof [Browning J. Y et al. 1983, Ho M. N. et al. 1997, Barbarino A et al. 1982, Imai, A et al. 1993, Kang, Sung K et al. 2000 et 2001, Gründker C et al. 2003, Leung P. C. K et al. 2003, Bhasin S. et al. 2008].

According to one preferred embodiment, peptides described herein are useful as inhibitors of IGF-1 activity and/or are capable of targeting cells expressing IGF-1 and/or IGF-1 receptors. More particularly, peptides of the invention are useful in an efficient dose to inhibit IGF-1 synthesis and/or expression of IGF-1 receptor. One particular aspect of the invention is the use of peptides as described above for inhibition of cell proliferation in vitro, for example in keratocytes, chondrocytes or hepatocytes cultures.

With these remarkable properties, peptides described herein are useful in human or veterinary medicine.

Inhibition of IGF-1 synthesis and/or expression of IGF-1 receptor is desired in a variety of diseases.

For instance, the peptides may be used as a somatostatin's substitute, in various disorders like those for which octreotide and lantreotide are indicated. The desired biological effects are for instance inhibition of pituitary GH secretion, inhibition of biliary secretion, inhibition of pancreatic and gastrointestinal exocrine and/or endocrine secretions. For example, peptides are used as somatostatin's substitute for treatment of Alzheimer's disease.

The peptides are also useful for treatment of acromegaly, particularly in patients who have had an inadequate response to surgery, and/or radiation therapy, and other medical therapies, or for whom these therapies are not appropriate. The goal of treatment is then to normalize serum IGF-1 levels and to improve clinical signs and symptoms.

In another embodiment, peptides described herein are used in treatment of cancer. Different types of treated cancer may include, but are not limited to: pituitary adenoma, breast cancer, pancreatic cancer, prostatic cancer, digestive endocrine tumor. Peptides are also useful to improve the symptoms associated with cancer such as diarrhea and flush.

Furthermore, peptides may be used for the treatment of metastases, including gastrointestinal metastasis.

Pharmaceutical Compositions:

The peptide may be administered by any convenient route including intravenous, oral, transdermal, subcutaneous, mucosal, intramuscular, intrapulmonary (see Agu et al, 2001), intranasal, parenteral, rectal, vaginal and topical. In a preferred embodiment, the agent is administered by intranasal route.

The dosing is selected by the skilled person so that an inhibitory effect with respect to IGF-1 synthesis and/or IGF-1 R expression is achieved.

An efficient dose to inhibit IGF-1 synthesis and/or expression of IGF-1 receptor in vivo typically includes a concentration of at least 30 μg daily, preferably from about 30 μg to 3 mg, depending on the administration route. Preferably, for administration via intranasal route the efficient daily dosage is from about 30 μg to 300 μg (see US2009/035260; Veronesi et al). Preferably, for other administration route, the efficient daily dosage is at least 300 μg daily, preferably from about 300 μg to 3 mg (corresponding to 109 to 1090 nM), more preferably efficient daily dosage is from about 1 mg to 3 mg, and still more preferably efficient daily dosage is from about 2 mg to 3 mg. The doses shall be adapted if sustained-release formulations are used.

Further aspects and advantages of the present invention will be disclosed in the following experimental section, which should be regarded as illustrative and not limiting the scope of the present application.

The peptide sequence, used in following examples and figures,—named P7—contains the following amino acids sequence:

```
                                          (SEQ ID NO: 2)
Acetyl-G-T-S-D-R-V-Y-E-K-L-A-G-S-K-N-F-F-W-K-T-F-
T-S-S
```

LEGENDS TO THE FIGURES

EXAMPLES

Administered by subcutaneous route to female rats peptide P7 induced antagonist and/or agonist GH effects without inducing, nevertheless, anti-peptide antibody. These results allowed inventors to assume that the peptide might have its own particular biological activity, so peptide effects in an in vitro model is checked in primary neonatal mouse mandibulary chondrocyte culture and cellular proliferation is studied, IGF-I synthesis and IGF-IR expression.

Materials and Methods

Cell Culture

P7 was tested in vitro in a model of endochondral ossification using a primary neonatal mouse mandibulary chondrocyte culture (Reiter et al, 2002). Peptide was present within cell culture throughout incubation period (5 days) and medium was changed every 48 hours supplemented with fresh peptide. Thymidine incorporation into DNA was checked after 48 hr in culture. Levels of IGF-I and of IGF-IR expression were checked on the $5^{th}$ day.

IGF-I and IGF-IR Expression

Levels of IGF-I synthesis and of IGF-I receptor (IGF-IR) expression were checked by immunoblotting and immunohistochemistry as described in Goldberg et al.

Results

Figure 1:
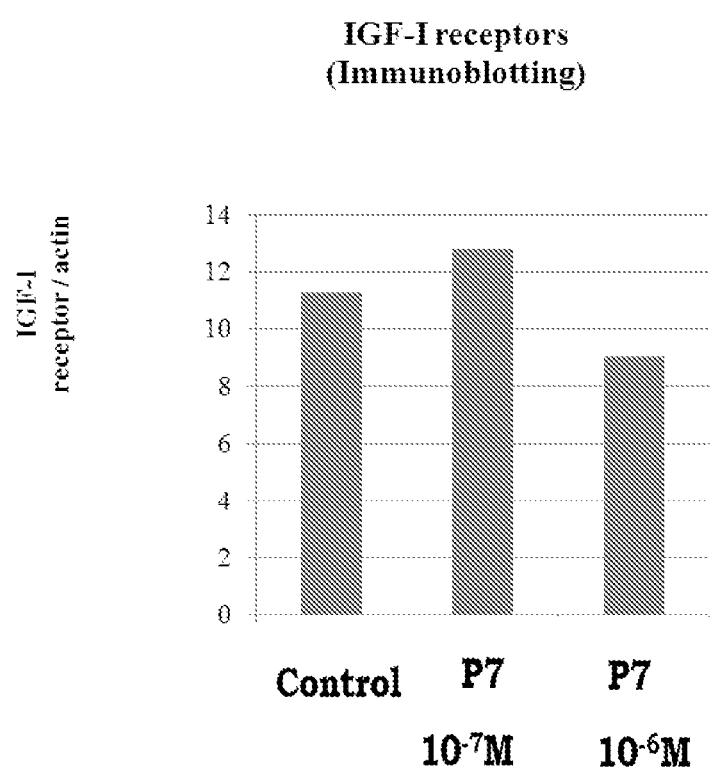
FIG. 1 is a graph that shows P7 effect on IGF-1 R expression (Immunoblotting)
Figure 2:
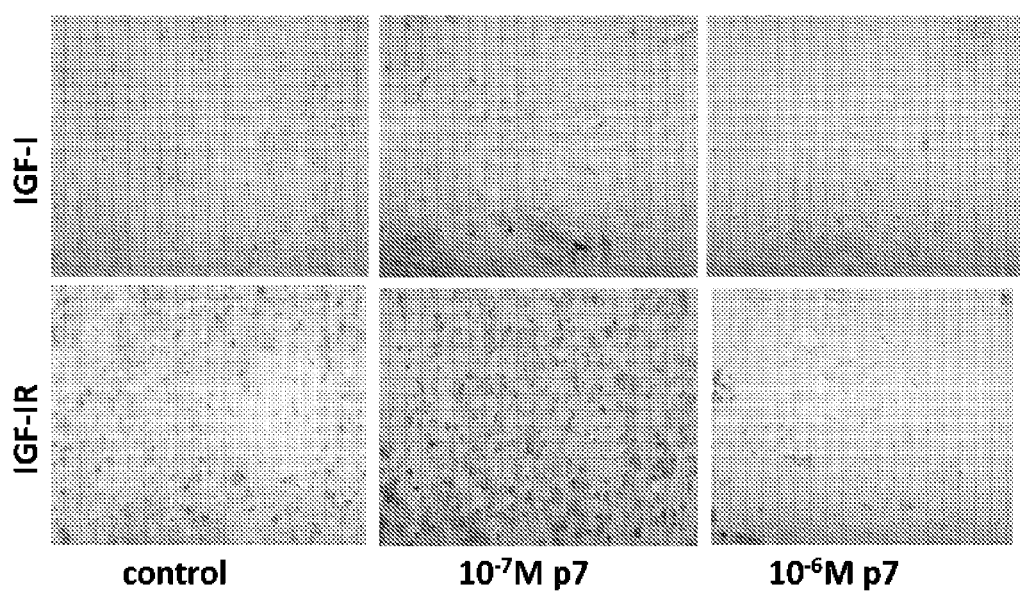
FIG. 2 shows an immunohistochemistry analysis of P7 effect on IGF-1 and IGF-1R expression

FIG. 1 illustrates that 5 days incubation of primary neonatal mouse mandibulary chondrocyte culture in the presence of $10^{-6}$ M of P7 induces a biphasic effect on IGF-IR. Immunohistochemistry staining depicted clearly in FIG. 2 that while $10^{-7}$ M P7 simulated the expression of both IGF-I and IGF-IR, $10^{-6}$ M P7 markedly suppresses the expression of these factors. Quantification of immunohistochemistry staining was performed by densitometry: IGF-I level when P7 is at low concentration ($10^{-7}$ M) is +65% and when P7 is at high concentration ($10^{-6}$ M) is −15%.

Conclusion

In vitro administration of this peptide resulted in a dual effect, in a low dose ($10^{-7}$ M) there was an accelerating effect on the IGF-I/IGF-IR axis the major local regulator of chondrogenesis, whereas a high P7 dose ($10^{-6}$ M) had an inhibitory effect.

REFERENCES

Arias H R: (1996) Agonist self-inhibitory binding site of the nicotinic acetylcholine receptor. J Neurosci Res, 44:97-105.

Agu R U, Ugwoke M I, Armand M, Kinget R, Verbeke N. The lung as a route for systemic delivery of therapeutic proteins and peptides. *Respir Res.* 2001; 2(4):198-209. Epub 2001 Apr. 12

Barbarino A, De Marinis L., Mancini A., Giustacchini M., Alcini A. E. (1982) Biphasic effect of estradiol on luteinizing hormone response to gonadotropin-releasing hormone in castrated men, Metabolism 31(8):755-8

Bhasin S, Heber D, Steiner B, Peterson M, Blaisch B, Campfield L A, Swerdloff R. S. (2008) Hormonal effects of GnRH agonist in the human male: II. Testosterone enhances gonadotrophin suppression induced by GnRH agonist. Clinical Endocrinologyy 20: 119-128

Bjorndahl M. et al. (2005). "Insulin-like growth factor 1 and 2 induce lymphangiogenesis in vivo. PNAS USA 102, 15593-15598.

Borst P, Elferink R O: Mammalian ABC transporters in health and disease. Annu Rev Biochem 2002, 71:537-592.

Bronnikov G E, Zhang S J, Cannon B, Nedergaard J (1999) A dual component analysis explains the distinctive kinetics of cAMP accumulation in brown adipocytes. J Biol Chem, 274:37770-37780.

Browning J. Y., R. D'Agata, A. Steinberger, H. E. Grotjan Jr and E. Steinberger (1983) Biphasic effect of gonadotropin-releasing hormone and its agonist analog (HOE766) on in vitro testosterone production by purified rat Leydig cells, Endocrinology, Vol 113, 985-991

Camirand A. Zakikhani M, Young F, Pollak M. (2005). "Inhibition of insulin-like growth factor-1 receptor signalling enhances growth-inhibitory and proapoptotic effects of gefitinib (Iressa) in human breast cancer cells". Breast Cancer Res. 7, R570-579.

Cassoni P. et al. (2006). "Grelin and cortistatin in lung cancer: expression of peptides and related eceptors in human primary tymors in vitro effect on the H345 small cell carcinoma cell line". J. Endocrinol. Invest. 29, 781-790.

Chidiac P, Nouet S, Bouvier M (1996) Agonist-induced modulation of inverse agonist efficacy at the beta 2-adrenergic receptor. Mol Pharmacol, 50:662-669.

Chinnavian P. et al. (2006). "Radiation and new molecular agents, pert II: targeting HDAC, HSPçà, IGF-1R, PI3K, and Ras". Semin. Radiat. Oncol. 16, 59-64.

Colòn E. et al. (2007). Insulin-like growth factor-I is an important antiapoptotic factor for rat leydig cells during postnatal development. Endocrinology 148, 128-139.

Cuthbert A W: (2003) Benzoquinolines and chloride secretion in murine colonic epithelium. Br J Pharmacol, 138: 1528-1534.

Dasgupta 2004, (2004) <<Somatostatin analogues: multiple roles in cellular proliferation, neoplasia, and angiogenesis>> Pharmacol Ther 102 (1): 61-85

Deutsch E. et al. (2005). "New strategies to interfere with radiation response: "biomodulation" of radiation therapy". Cancer Radiother. 9, 69-76.

Ferjoux G., C. Bousquet, P. Cordelier et al. (2000). "Signal transduction of somatostatin receptors negatively controlling cell proliferation". J. Physiol. (Paris) 94, 205-210.

Fuh G, Cunningham B C, Fukunaga R, Nagata S, Goeddel D V, Wells J A (1992) Rational design of potent antagonists to the human growth hormone receptor. Science, 256:1677-80.

Gamage N U, Duggleby R G, Barnett A C, Tresillian M, Latham C F, Liyou N E, McManus M E, Martin J L (2003) Structure of a human carcinogen-converting enzyme, SULT1A1. Structural and kinetic implications of substrate inhibition. J Biol Chem, 278:7655-7662

Garcia de la Torre N, Wass J A, Turner H E, (2002) <<Antiangiogenic effects of somatostatin analogues" Clin Endocrinol 2002 57(4): 425-441 Review Gennigens C., C. Menetrier-Caux, J. P. Droz (2006). "Insulin-like growth factor (IGF) family and prostate cancer". Crit. Rev. Oncol. Hematol. 58, 124-145

Goldberg R, Ella Reshef-Bankai, Coleman R, Green J, Maor G "Chronic acidosis-induced growth retardation is mediated by proton-induced expression of Gs protein" J Bone and Mineral Research 2006 21 (5): 703-713

Griffin M T, Hsu J C, Shehnaz D, Ehlert F J: Comparison of the pharmacological antagonism of M2 and M3 muscarinic receptors expressed in isolation and in combination. Biochem Pharmacol 2003, 65:1227-1241.

Gründker C. and G. Emons (2003) Role of gonadotropin-releasing hormone (GnRH) in ovarian cancer. Reproductive Biology and Endocrinology 1:65

Hanahan D., R. A. Weinberg (2000). "The hallmarks of cancer". Cell 100, 57-70.

He Y A, Roussel F, Halpert J R (2003) Analysis of homotropic and heterotropic cooperativity of diazepam oxidation by CYP3A4 using site-directed mutagenesis and kinetic modeling. Arch Biochem Biophys, 409:92-101.

Henry E R, Bettati S, Hofrichter J, Eaton W A (2002) A tertiary two-state allosteric model for hemoglobin. Biophys Chem, 98:149-164.

Ho M. N.; Delgado C. H., Owens G. A., Steller M. A. (1997) Insulin-like growth factor-II participates in the biphasic effect of a gonadotropin-releasing hormone agonist on ovarian cancer cell growth, Fertility and Sterility Volume 67, Number 5, May 1997, pp. 870-876(7)

Hofmann F., C. Garcia-Echeverria (2005). "Blocking insulin-like growth factor-I receptor as a strategy for targeting cancer". DDT 10, 1041-1047.

Hornigold D C, Mistry R, Raymond P D, Blank J L, Challiss R A (2003) Evidence for cross-talk between M2 and M3 muscarinic acetylcholine receptors in the regulation of second messenger and extracellular signal-regulated kinase signalling pathways in Chinese hamster ovary cells. Br J Pharmacol, 138:1340-1350.

Imai, A, Iida, K, Tamaya, T (1993) Gonadotropin-releasing hormone has a biphasic action on aromatase activity through protein kinase C in granulosa cells. Int-J-Fertil-Menopausal-Stud. 38(1): 50-56

Incerpi S, D'Arezzo S, Marino M, Musanti R, Pallottini V, Pascolini A, Trentalance A (2003) Short-term activation by low 17beta-estradiol concentrations of the Na+/H+ exchanger in rat aortic smooth muscle cells: physiopathological implications. Endocrinology, 144:4315-4324.

Inoue A. et al. (2005). "Insulin-growth factor-I stimulated DNA replication in mouse endometrial stromal cells". J. Reprod. Dev. 51, 305-313.

Kambhampati S. et al. (2005). "Growth factors involved in prostate carcinogenesis". Front. Biosci. 10, 1355-1367.

Kang, Sung K.; Cheng, Kwai W.; Nathwani, Parimal S.; Choi, Kyung-Chul; Leung, Peter C. K. (2000) Autocrine Role of Gonadotropin-Releasing Hormone and Its Receptor in Ovarian Cancer Cell Growth. Endocrine. 13(3):297-304

Kang S. K., C-J Tai, P S. Nathwani and P. C. K. Leung (2001) Differential regulation of two forms of Gonadotrophin-related hormone messenger ribonucleic acid in human granulosa-luteal cells. Endocrinology 142: 1182-1192

Kucab J. E., S. E. Dunn (2003). "Role of IGF-1R in mediating breast cancer invasion and metastasis". Breast Dis. 17, 41-47

Kurz B, Schünke M, (1997) <<Articular chondrocytes and synoviocytes in culture: influence of antioxidants on lipid peroxidation and proliferation." Ann. Anat. 1997, 179: 439-446

Laron Z. (2001). "Insulin-like growth factor 1 (IGF-1): a growth hormone". J. Clin. Pathol. Mol. Pathol. 54, 311-316.

Lehninger, (1975) Biochemistry, Second Edition, Worth Publishers, Inc. New-York: N.Y., pp. 71-77.

Leiser J, Conn P M, Blum J J: (1986) Interpretation of dose-response curves for luteinizing hormone release by gonadotropinreleasing hormone, related peptides, and leukotriene C4 according to a hormone/receptor/effector model. Proc Natl Acad Sci USA, 83:5963-7.

Leung P. C. K., C. K. Cheng and Z. Xiao-Ming (2003) Multifactorial role of GnRH-I and GnRH-II in the human ovary. Molecular and Cellular Endocrinology 202: 145-153

Lombardi G, Dianzani C, Miglio G, Canonico P L, Fantozzi R: Characterization of ionotropic glutamate receptors in human lymphocytes. Br J Pharmacol 2001, 133:936-944.

Min Y. et al. (2005). "Insulin_like growth factor I receptor blockade enhances chemotherapy and radiation responses and inhibits tumor growth in human gastric cancer xenografts". Gut 54, 591-60.

Moyse E. et al. (1985). "Somatostatin receptors in human growth hormone and prolactin-secreting pituitary adenomas". J. Clin. Endocrinol. Metab. 61, 98-103.

Pandit A., fay N., Border L, Valéry C., Cherif-Cheikh R., Robert B., Artzner F., Paternoster M. J. (2008) Pept. Sci., 14, 66-75.

Pawlikowski M. et Malen-Mucha G. Current Opinion in Pharmacology (2004), 4, 608-613.

Perona R. (2006). "Cell signaling: growth factors and tyrosine kinase receptors". Clin. Transl. Oncol. 8, 77-821.

Rani C., Durrer L., Koerber S. C., Erchegyi J., Reubi J. C., Rivier J., Riek R. J. Med. Chem. (2004), 48, 523-533

Rani C., Durrer L., Koerber S. C., Erchegyi J., Reubi J. C., Rivier J., Riek R. J. Med. Chem. (2006), 49, 4487-4496

Reiter I, Tzukerman et Maor, <<spontaneous differentiating primary tissue culture: a model for endochondral ossification. Bones, 31, 333-339.

Samani A. A. et al. (2007). "The Role of the IGF System in Cancer Growth and Metastasis: Overview and Recent Insights". Endocrine Reviews 28, 20-47.

Schlessinger J (1998) Signal transduction by allosteric receptor oligomerization. Trends Biochem Sci, 13:443-447.

Shevah O., Z. Laron (2007). "Patients with congenital deficiency of IGF-I seem protected from the development of malignancies: A preliminary report". Growth Horm IGF Res. 17, 54-57.

Sisci D., E. Surmacz (2007). "Crosstalk between IGF Signaling and Steroid Hormone Receptors in Breast". Cancer Curr. Pharm. Des. 13, 705-717.

Talapatra S., C. B. Thmpson (2001). "Growth factor Signaling in Cell Survival: Implications for Cancer". Treatment JPET, 298, 873-878.

Talmadge J E (1998) Pharmacodynamic aspects of peptide administration biological response modifiers. Adv Drug Deliv Rev, 241-252

Velcheti V, Govindan R (2006). "Insulin-like growth factor and lung cancer". Journal of thoracic oncology: official publication of the International Association for the Study of Lung Cancer 1 (7): 607-10.

Vella V. et al. (2001). "The IGF system in thyroid cancer: new concepts". J. Clin. Pathol.: Mol. Pathol. 54, 121-125

Warshamana-Greene G. S. et al. (2005). "The insulin-like growth factor-I receptor kinase inhibitor, NVP-ADW742, sensitized small cell lung cancer cell lines to the effects of chemotherapy". Clin. Cancer. Res. 11, 1563-1571.

Winding B, Bindslev N (1993) Desensitization and reactivation of ACh-regulated exocrine secretion in hen tracheal epithelium. Am J Physiol, 264:C342-C351.

Wu X. Z., D. Chen, G. R. Xie (2007). "Bone marrow-derived cells: roles in solid tumor". Neoplasma 54, 1-6.

Yanochko G. M., W. Eckhart (2006). "Type I insulin-like growth factor receptor overexpression induces proliferation and anti-apoptotic signaling in a three-dimensional culture model of breast epithelial cells". Breast Cancer Res. 8, R18.

The invention claimed is:

1. A method for inhibiting growth of chondrocytes in a subject, the method comprising administering to a subject in need thereof a therapeutically effective amount of a peptide comprising the amino acid sequence of SEQ ID NO: 2 or
a proteolysis-resistant peptide deriving from SEQ ID NO: 2 by one or more chemical modifications.

2. The method according to claim 1, wherein one or more of amino acids threonine, alanine, tryptophan, and phenylalanine of SEQ ID NO: 2 are in D form.

3. The method according to claim 2, wherein the consecutive phenylalanine residues in SEQ ID NO: 2 are in D form.

4. The method according to claim 1, wherein a $C_1$-$C_3$ alkyl group is covalently bound to the tryptophan residue of SEQ ID NO: 2.

5. The method according to claim 1, wherein the peptide is covalently bound to poly(ethyleneglycol) by the C-terminal terminus or a lysine residue.

6. An in vitro method of inhibiting chondrocyte proliferation, the method comprising contacting a chondrocyte with the peptide of claim 1.

7. The method according to claim 1, wherein the subject suffers from acromegaly.

8. The method according to claim 1, wherein the peptide is administered at a dose of at least 30 μg daily.

9. The method according to claim 2, wherein the peptide is administered at a dose of at least 30 μg daily.

10. The method according to claim 3, wherein the peptide is administered at a dose of at least 30 μg daily.

11. The method according to claim 4, wherein the peptide is administered at a dose of at least 30 μg daily.

12. The method according to claim 1, wherein the one or more chemical modifications to the peptide comprising the amino acid sequence of SEQ ID NO: 2 are modification of the N-terminal end in the form of an acetyl, the C-terminal end in the form of an amide group, or at least one peptide bond being replaced with a ($CH_2NH$) bond, an (NHCO) bond, a ($CH_2$—O) bond, a ($CH_2$—S) bond, a ($CH_2CH_2$) bond, a (CO—$CH_2$) bond, a (CHOH—$CH_2$) bond, an (N—N) bond, an E-alkene bond, or a —CH=CH bond.

13. The method according to claim 5, wherein the peptide is administered at a dose of at least 30 μg daily.

* * * * *